United States Patent [19]

Witzke

[11] 4,396,610
[45] Aug. 2, 1983

[54] WATER-SOLUBLE GUANIDINE DERIVATIVES OF POLYENE MACROLIDES AND THE ESTERS THEREOF, AND PROCESS FOR PREPARATION THEREOF

[75] Inventor: Niels Witzke, New Brunswick, N.J.

[73] Assignee: A/S Dumex (Dumex Ltd.), Copenhagen S, Denmark

[21] Appl. No.: 219,537

[22] Filed: Dec. 23, 1980

[30] Foreign Application Priority Data

Dec. 24, 1979 [GB] United Kingdom ................ 7944360

[51] Int. Cl.³ ...................... A61K 31/71; C07H 17/08
[52] U.S. Cl. ...................................... 424/180; 536/6.5
[58] Field of Search ........... 424/180; 536/17 R, 17 C, 536/6.5

[56] References Cited

U.S. PATENT DOCUMENTS 3,945,993 3/1976 Schaffner et al. ................ 536/17 C
3,957,754 5/1976 Aszalos et al. .................... 536/17 C
4,195,172 3/1980 Falkowski et al. ............... 536/17 R
4,272,525 6/1981 Wright ............................. 536/17 R Primary Examiner—Johnnie R. Brown
Attorney, Agent, or Firm—Wenderoth, Lind & Ponack

[57] ABSTRACT

New guanidine derivatives of polyene macrolides having at least one free amino group and at least one free carboxy group (e.g. nystatin, pimaricin, amphotericin B, candicidin and trichomycin) are prepared by reacting the macrolide with a carbodiimide of the formula:

$$R^1-N=C=N-R^2$$

wherein $R^1$ and $R^2$ are independently alkyl, substituted alkyl, cycloalkyl, aralkyl, aryl or aroylalkyl. Esters and salts of the derivatives can also be formed. The new derivatives are water-soluble and can be used as antimycotic agents.

6 Claims, No Drawings

WATER-SOLUBLE GUANIDINE DERIVATIVES OF POLYENE MACROLIDES AND THE ESTERS THEREOF, AND PROCESS FOR PREPARATION THEREOF

The present invention relates to new guanidine derivatives of polyene macrolides, for example nystatin, pimaricin, amphotericin B, candicidin and trichomycin and the esters thereof, and a process for preparing these derivatives.

Thus according to the present invention there is provided a process for the preparation of a guanidine derivative of a polyene macrolide or an ester thereof which comprises reacting a polyene macrolide containing at least one free amino group and at least one free carboxy group with a carbodiimide of the formula:

$$R^1-N=C=N-R^2 \quad \text{I}$$

(wherein $R^1$ and $R^2$, which may be the same or different, each represents a substituted or unsubstituted straight chain or branched alkyl group, a cycloalkyl group, aralkyl, aryl or aroylalkyl group) or, where appropriate, with a salt thereof.

Where it is desired to obtain the said guanidine derivative in the form of an ester thereof, the reaction is conveniently effected in the presence of a hydroxy compound of the formula:

$$ROH \quad \text{II}$$

(wherein R represents a straight chain or branched alkyl group optionally substituted by a halogen atom or by a heterocyclic or functional group; a cycloalkyl group, an aralkyl group or an aryl group).

As stated above the polyene macrolide used as starting material is an antibiotic such as, for example, nystatin, pimaricin, amphotericin B, candicidin or trichomycin. In this connection the water-soluble guanidine derivatives of polyene macrolides, containing at least one free amino group and at least one free carboxyl group, and the esters thereof are of interest as anti-mycotic agents and have in general been found to possess a lower toxicity than the corresponding parent compound when administered to mice intraperitoneally.

Thus the well known amphotericin B is injected intravenously only. Notwithstanding its toxicity it has been considered the antibiotic of choice in the treatment of systemic mycoses until now. The methylester of amphotericin B, described in U.S. Pat. No. 3,945,993, is less toxic but can likewise be injected intravenously only, which results in a very rapid excretion. The guanidine derivative of amphotericin which is one of the objects of the present invention, is firstly less toxic and secondly, it has very surprisingly been found that it can be injected via the intramuscular route whereby the beneficial anti-infective effect is prolonged.

The guanidine derivatives of the present invention can be administered to human patients both by oral, intramuscular and intravenous route in the treatment of systemic mycoses.

The daily effective dose of the polyene macrolides depends upon the condition being treated, the individual characteristics of the patient as well as on the particular polyene macrolide being used.

Generally, the oral dosage range is from about 400 mg up to 10 grams per day, preferably from about 400 mg up to 5 grams a day, while the intramuscular and intravenous dosage range is between one and ten milligrams per kilogram body weight per day, preferably between two and five milligrams per kilogram body weight per day.

Pharmacology/Toxicology

1-Dimethylaminopropyl 3-ethyl carbodiimide amphotericin B (DAPEG-AB), minimum fractionary inhibition (MFI) against fungi, compared with amphotericin B (AB).

| Organism | MFI, mcg/ml | |
|---|---|---|
| | AB | DAPEG—AB |
| Candida albicans 1. | 0.63 | 3.90 |
| Candida albicans 2. | 1.30 | 1.30 |
| Aspergillus niger | 3.20 | 2.40 |
| Paecilomyces varioti | 0.79 | 0.96 |

Comparison of acute toxicity, administered intravenously to mice (CFI, males).

| | Dose, mg/kg | Mortality, 1 day | Time of death |
|---|---|---|---|
| AB | 3.5 | ⅜ | Less than 2 min. |
| | 4.2 | 6/8 | |
| DAPEG—AB | 32 | ⅛ | 1 to 3 hours |
| | 38 | 4/8 | |
| | 44 | ⅝ | |

In the carbodiimide of formula I $R^1$ and $R^2$, which may be the same or different, may for example each represent an alkyl group with 1–6 carbon atoms optionally substituted by, for example, a secondary or tertiary amine grouping, e.g. a dialkylamino group such as a $C_{2-12}$ dialkylamino group, e.g. a dimethylamino group or by a heterocyclic grouping, e.g. a 5–7 membered heterocyclic grouping such as a morpholino, pyrrolidino, or piperidino group optionally substituted by $C_1$–$C_6$ alkyl. Thus $R^1$ or $R^2$ may contain a tertiary amino group or a quaternary ammonium grouping. Thus, for example, $R^1$ may represent an alkyl group, e.g. with 1–6 carbon atoms, substituted by a secondary or tertiary amino group, e.g. as described above, while $R^2$ represents an unsubstituted alkyl or cycloalkyl group. Where $R^1$ and/or $R^2$ represent a cycloalkyl group, such group preferably contains 3–7, e.g. 5 or 6, carbon atoms. Where $R^1$ and/or $R^2$ represent an aralkyl, aryl or aroylalkyl group, the aryl group or moiety may, for example, contain 6–10 carbon atoms and the alkyl moiety may, for example, contain 1–6 carbon atoms. Where the compound of formula I is used in the form of a salt, e.g. in the form of a quaternary ammonium salt contained in $R^1$ and/or $R^2$, the stabilizing anion may be any convenient anion, e.g. a halide such as a chloride or an arylsulfonate such as a toluenesulfonate, e.g. a p-toluenesulfonate.

Where the group R in the compound of formula II represents or contains an alkyl group, said group may have, for example, 1–6 carbon atoms. Where R represents a cycloalkyl group, said group may contain, for example, 3–7, e.g. 5 or 6, carbon atoms, and where R represents an aralkyl group, said group may contain, for example, 7–10 carbon atoms. Aryl groups may contain, for example, 6–10 carbon atoms. Haloalkyl groups include, for example, chloroalkyl and bromoalkyl groups. Where R represents an alkyl group substituted by a heterocyclic nucleus, the heterocyclic nucleus may, for example, be a 5-7 membered heterocyclic grouping such as a morpholino, pyrrolidino, or piperidino group.

Where R represents an alkyl group substituted by a functional group, the functional group may, for example, be a halogen atom, e.g. chlorine or bromine, or a hydroxy, amino, keto or carboxy group.

It is advantageous to effect the reaction at or below room temperature, e.g. 0°-10° C., preferably in the presence of N-methylpyrrolidone, hexamethylphosphoric acid amide, or a mixture of hexamethylphosphoric acid amide and tetramethylurea.

In order to avoid esterification of the carboxylic acid group of the polyene macrolide, where this is desired, it is advantageous to carry out the preparation of the guanidine type derivative in the presence of up to 10% of water.

Where it is desired to prepare the ester, the reaction is advantageously effected in the presence of an acid, e.g. up to one equivalent of an acid, preferably an acid which is not or which is only slowly esterified by hydroxy compounds, for example an organic sulfonic acid, a Lewis acid or an inorganic acid.

The esterification reaction may, for example, be effected in the presence of a mixture of the hydroxy compound and a solvent in which the polyene macrolide shows good solubility.

The present invention also provides a derivative of a polyene macrolide which contains at least one free carboxy group and at least one guanidino group of the formula:

—NH—C(NHR$^1$)=NR$^2$ (wherein R$^1$ and R$^2$, which may be the same or different, each represents an alkyl, cycloalkyl, aralkyl, aryl or aroylalkyl group), and the pharmaceutically acceptable esters and salts thereof; and a pharmaceutical composition comprising this derivative and a pharmaceutically acceptable carrier therefor.

The invention is illustrated by the following examples:

EXAMPLE 1

1-Dimethylaminopropyl 3-ethyl carbodiimide amphotericin B hydrochloride 40 mg of amphotericin B, 0.01 ml of a 20% solution of butylhydroxytoluene in tetrahydrofuran, and 0.018 ml 20% 1-methylimidazole in tetrahydrofuran are dissolved in 1 ml of a mixture of equal parts of hexamethylphosphoric acid amide and tetramethylurea. When all the substances have dissolved, 0.1 ml water and 9 mg of 1-dimethylaminopropyl 3-ethyl carbodiimide hydrochloride are added, and the mixture is stirred for 3-4 days under an atmosphere of argon at 6°-8° C. The reaction is monitored by thin layer chromatography (TLC) (see below). The pH should be in the range 6.5-8 and is estimated in 0.025 ml of the reaction mixture diluted with 0.4 ml of argonized water.

The reaction mixture is diluted with 15 ml of acetone, and centrifuged at 6° C. The supernatant is collected, concentrated in vacuo, and added to 20 ml of diethyl ether while stirring vigorously. The mixture is stirred for 1 hour in an ice box. The precipitate is recovered by filtration and washed with diethyl ether. After drying in vacuo over concentrated sulfuric acid, 20 mg of 1-dimethylaminopropyl 3-ethyl carbodiimide amphotericin B hydrochloride is obtained as a light yellow powder.

E 1% (382 nm, MeOH): 1320

IR: 1650-1700 cm$^{-1}$: C=N stretching band

No absorption at 1400 cm$^{-1}$: no primary amino group.

TLC-system

Tetrahydrofuran and 0.7 M ammonia (4:1)
Silica gel TLC-plates
Rf: 0.36, the derivative
Rf: 0.28, amphotericin B.

EXAMPLE 2

1-(N-methylmorpholiniumethyl)-3-cyclohexyl carbodiimide amphotericin B methylester di-p-toluenesulfonate 40 mg of amphotericin B is dissolved in a mixture of 0.4 ml of hexamethylphosphoric acid amide, 0.1 ml of tetramethylurea and 0.01 ml of a 20% solution of butylhydroxytoluene in tetrahydrofuran. To this solution 47 mg of 1-(N-methylmorpholiniumethyl)-3-cyclohexyl carbodiimide p-toluenesulfonate, 0.5 ml of anhydrous methanol, and 0.025 ml of 2 M pyridine p-toluenesulfonate in methanol is added. The mixture is stirred at 6°-8° C. for 17 hours under an atmosphere of argon. A further 10 mg of 1-(N-methylmorpholiniumethyl)-3-cyclohexyl carbodiimide p-toluenesulfonate is added, stirring at 6°-8° C. under an atmosphere of argon being continued for an additional 54 hours. The reaction is monitored by TLC (see below). The pH was determined by diluting 0.025 ml of the reaction mixture with 0.4 ml of argonized water, and is found to increase from 4.4 to 6.0 during the reaction.

The solution is mixed with 5 ml of acetone, centrifuged at 6° C., and 0.002 ml tributylamine is added to the supernatant, followed by 12 ml of dry ethyl ether; the precipitate is centrifuged and washed twice with 10 ml of ethyl ether. After drying in vacuo over concentrated sulfuric acid, 30 mg of 1-(N-methylmorpholiniumethyl)-3-cyclohexyl carbodiimide amphotericin B methylether di-p-toluenesulfonate is obtained. The H$^1$-NMR (d$_6$-DMSO) shows a singlet at 67 =3.7 ppm (—COOCH$_3$). IR: 1650-1700 cm$^{-1}$: C=N stretching band No absorption at 1400 cm$^{-1}$: no primary amino group.

TLC-system

Tetrahydrofuran, methanol and 5% aqueous ammoniumcarbonate (3:1:1).
Silica gel TLC-plate.
Rf: 0.78, amphotericin methylester.
Rf: 0.30, amphotericin B.
Rf: 0.13, the guanidine type derivative methyl ester.
Rf: 0.06, the guanidine type derivative.

I claim:

1. The hydrochloride of the guanidino type derivative of 1-dimethylaminopropyl-3-ethyl carbodiimide hydrochloride with amphotericin B, said guanidino type derivative containing at least one guanidino group of the formula

—NH—C(NHR$^1$)=NR$^2$ wherein R$^1$ and R$^2$, which may be the same or different, are selected from the group consisting of (1) alkyl of 1-6 carbon atoms, (2) alkyl of 1-6 carbon atoms substituted by dialkylamino of 2-12 carbon atoms, morpholino, morpholino substituted by alkyl of 1-6 carbon atoms, pyrrolidino, pyrrolidino substituted by alkyl of 1-6 carbon atoms, piperidino, or piperidino substituted by alkyl of 1–6 carbon atoms, (3) cycloalkyl of 3–7 carbon atoms, (4) aralkyl of 6–10 carbon atoms in the aryl moiety and 1–6 carbon atoms in the alkyl moiety, (5) aryl of 6–10 carbon atoms, and (6) aroylalkyl of 6–10 carbon atoms in the aryl moiety and 1–6 carbon atoms in the alkyl moiety.

2. The methyl ester of the guanidino type derivative of 1-(N-methylmorpholiniumethyl)-3-cyclohexyl carbodiimide p-toluenesulfonate with amphotericin B, said guanidino type derivative containing at least one guanidino group of the formula $$-NH-C(NHR^1)=NR^2$$

wherein $R^1$ and $R^2$, which may be the same or different, are selected from the group consisting of (1) alkyl of 1–6 carbon atoms, (2) alkyl of 1–6 carbon atoms substituted by dialkylamino of 2–12 carbon atoms, morpholino, morpholino substituted by alkyl of 1–6 carbon atoms, pyrrolidino, pyrrolidino substituted by alkyl of 1–6 carbon atoms, piperidino, or piperidino substituted by alkyl of 1–6 carbon atoms, (3) cycloalkyl of 3–7 carbon atoms, (4) aralkyl of 6–10 carbon atoms in the aryl moiety and 1–6 carbon atoms in the alkyl moiety, (5) aryl of 6–10 carbon atoms, and (6) aroylalkyl of 6–10 carbon atoms in the aryl moiety and 1–6 carbon atoms in the alkyl moiety.

3. A pharmaceutical composition for treating systemic mycoses, comprising (A) a pharmaceutically effective amount of a member selected from the group consisting of the hydrochloride of the guanidino type derivative of 1-dimethylaminopropyl-3-ethyl carbodiimide hydrochloride with amphotericin B, and the methyl ester of the guanidino type derivative of 1-(N-methylmorpholiniumethyl)-3-cyclohexyl carbodiimide p-toluenesulfonate with amphotericin B, each of said guanidino type derivatives containing at least one guanidino group of the formula $$-NH-C(NHR^1)=NR^2$$

wherein $R^1$ and $R^2$, which may be the same or different, are selected from the group consisting of (1) alkyl of 1–6 carbon atoms, (2) alkyl of 1–6 carbon atoms substituted by dialkylamino of 2–12 carbon atoms, morpholino, morpholino substituted by alkyl of 1–6 carbon atoms, pyrrolidino, pyrrolidino substituted by alkyl of 1–6 carbon atoms, piperidino, or piperidino substituted by alkyl of 1–6 carbon atoms, (3) cycloalkyl of 3–7 carbon atoms, (4) aralkyl of 6–10 carbon atoms in the aryl moiety and 1–6 carbon atoms in the alkyl moiety, (5) aryl of 6–10 carbon atoms, and (6) aroylalkyl of 6–10 carbon atoms in the aryl moiety and 1–6 carbon atoms in the alkyl moiety, and (B) a pharmaceutically acceptable carrier therefor.

4. A process for preparing a guanidine derivative of a polyene macrolide or an ester thereof, which comprises reacting a polyene macrolide selected from the group consisting of nystatin, pimaricin, amphotericin B, candicidin and trichomycin, with a carbodiimide of the formula $$R^1-N=C=N-R^2$$

wherein $R^1$ and $R^2$, which may be the same or different, are selected from the group consisting of (1) alkyl of 1–6 carbon atoms, (2) alkyl of 1–6 carbon atoms substituted by dialkylamino of 2–12 carbon atoms, morpholino, morpholino substituted by alkyl of 1–6 carbon atoms, pyrrolidino, pyrrolidino substituted by alkyl of 1–6 carbon atoms, piperidino, or piperidino substituted by alkyl of 1–6 carbon atoms, (3) cycloalkyl of 3–7 carbon atoms, (4) aralkyl of 6–10 carbon atoms in the aryl moiety and 1–6 carbon atoms in the alkyl moiety, (5) aryl of 6–10 carbon atoms, and (6) aroylalkyl of 6–10 carbon atoms in the aryl moiety and 1–6 carbon atoms in the alkyl moiety, or with a quaternary ammonium salt of said carbodiimide, with the proviso that when said ester is to be prepared, said reaction is carried out in the presence of a hydroxy compound of the formula $$ROH$$

wherein R is selected from the group consisting of (1) alkyl of 1–6 carbon atoms, (2) alkyl of 1–6 carbon atoms substituted by halogen, morpholino, pyrrolidino, piperidino, hydroxy, keto or carboxy, (3) cycloalkyl of 3–7 carbon atoms, (4) aralkyl of 7–10 carbon atoms, and (5) aryl of 6–10 carbon atoms.

5. A process according to claim 4, wherein said polyene macrolide is amphotericin B, and said carbodiimide is 1-dimethylaminopropyl-3-ethyl carbodiimide or 1-(N-methylmorpholiniumethyl)-3-cyclohexyl carbodiimide p-toluenesulfonate.

6. A process according to claim 4 or 5, wherein said reaction is carried out in methanol to prepare the methyl ester of said guanidine derivative.

* * * * *